(12) United States Patent
Jasperson et al.

(10) Patent No.: US 10,413,272 B2
(45) Date of Patent: Sep. 17, 2019

(54) SURGICAL TOOL WITH FLEX CIRCUIT ULTRASOUND SENSOR

(71) Applicant: COVIDIEN LP, Mansfield, MA (US)

(72) Inventors: Keith E. Jasperson, Andover, MN (US); H. Aaron Christmann, White Bear Lake, MN (US); Michael R. Weisenberger, Minneapolis, MN (US)

(73) Assignee: COVIDIEN LP, Mansfield, MA (US)

( * ) Notice: Subject to any disclaimer, the term of this patent is extended or adjusted under 35 U.S.C. 154(b) by 696 days.

(21) Appl. No.: 15/063,654

(22) Filed: Mar. 8, 2016

(65) Prior Publication Data

US 2017/0258439 A1    Sep. 14, 2017

(51) Int. Cl.
*A61B 8/08*  (2006.01)
*A61B 8/12*  (2006.01)
*A61B 8/00*  (2006.01)

(52) U.S. Cl.
CPC .............. *A61B 8/0841* (2013.01); *A61B 8/12* (2013.01); *A61B 8/445* (2013.01)

(58) Field of Classification Search
CPC .......... A61B 8/0841; A61B 8/12; A61B 8/445
See application file for complete search history.

(56) References Cited

U.S. PATENT DOCUMENTS

| | | |
|---|---|---|
| 3,868,565 A | 2/1975 | Kuipers |
| 3,983,474 A | 9/1976 | Kuipers |
| 4,017,858 A | 4/1977 | Kuipers |
| 4,054,881 A | 10/1977 | Raab |
| 4,287,809 A | 9/1981 | Egli et al. |
| 4,314,251 A | 2/1982 | Raab |
| 4,328,548 A | 5/1982 | Crow et al. |
| 4,346,384 A | 8/1982 | Raab |
| 4,394,831 A | 7/1983 | Egli et al. |
| 4,396,885 A | 8/1983 | Constant |
| 4,613,866 A | 9/1986 | Blood |
| 4,710,708 A | 12/1987 | Rorden et al. |
| 4,737,794 A | 4/1988 | Jones |

(Continued)

FOREIGN PATENT DOCUMENTS

| | | |
|---|---|---|
| EP | 0 922 966 A2 | 6/1999 |
| WO | 94/04938 A1 | 3/1994 |

(Continued)

OTHER PUBLICATIONS

Written Opinon of the International Searching Authority and International Search Report issued in Appl. No. PCT/US17/16471 dated Apr. 27, 2017.

*Primary Examiner* — Michael T Rozanski

(57) ABSTRACT

A medical instrument includes a printed ultrasound sensor, a surface, at least one non-conductive material, and at least one pair of contacts. The ultrasound sensor includes an array of ultrasound transducers printed on a non-conductive surface of the medical instrument. The medical instrument contains multiple conductive and nonconductive layers. The at least one pair of contacts are electrically coupled to the ultrasound sensor and operably coupled to the conductive layer, the conductive layer coupled to a measurement device, which converts electrical signals from the ultrasound sensor into images displayed on a display unit. The location of the medical instrument can be visualized in real time on the display unit.

18 Claims, 7 Drawing Sheets

(56) References Cited

U.S. PATENT DOCUMENTS

| | | |
|---|---|---|
| 4,742,356 A | 5/1988 | Kuipers |
| 4,849,692 A | 7/1989 | Blood |
| 5,307,072 A | 4/1994 | Jones, Jr. |
| 5,377,678 A | 1/1995 | Dumoulin et al. |
| 5,600,330 A | 2/1997 | Blood |
| 5,646,525 A | 7/1997 | Gilboa |
| 5,729,129 A | 3/1998 | Acker |
| 5,744,898 A * | 4/1998 | Smith ............... B06B 1/064 310/334 |
| 5,752,513 A | 5/1998 | Acker et al. |
| 5,957,849 A | 9/1999 | Munro |
| 5,991,697 A | 11/1999 | Nelson et al. |
| 6,006,127 A | 12/1999 | Van Der Brug et al. |
| 6,569,098 B2 | 5/2003 | Kawchuk |
| 6,615,155 B2 | 9/2003 | Gilboa |
| 6,837,855 B1 | 1/2005 | Puech |
| 6,889,075 B2 | 5/2005 | Marchitto et al. |
| 7,233,820 B2 | 6/2007 | Gilboa |
| 7,615,015 B2 | 11/2009 | Coleman |
| 7,706,882 B2 | 4/2010 | Francischelli et al. |
| 7,917,312 B2 | 3/2011 | Wang et al. |
| 7,967,742 B2 | 6/2011 | Hoeg et al. |
| 8,183,745 B2 | 5/2012 | Trolier-McKinstry et al. |
| 8,197,413 B2 * | 6/2012 | Kurse ............... A61B 8/12 29/594 |
| 9,247,992 B2 | 2/2016 | Ladtkow et al. |
| 2004/0193057 A1 | 9/2004 | Barbato et al. |
| 2004/0221853 A1 | 11/2004 | Miller |
| 2005/0143662 A1 | 6/2005 | Marchitto et al. |
| 2005/0217381 A1 | 10/2005 | Falk |
| 2006/0036162 A1 | 2/2006 | Shahidi et al. |
| 2006/0184042 A1 | 8/2006 | Wang et al. |
| 2007/0239007 A1 | 10/2007 | Silverman et al. |
| 2009/0088634 A1 | 4/2009 | Zhao et al. |
| 2009/0216129 A1 | 8/2009 | Lasser et al. |
| 2009/0287223 A1 | 11/2009 | Pua et al. |
| 2009/0318756 A1 | 12/2009 | Fisher et al. |
| 2011/0106052 A1 | 5/2011 | Chiang et al. |
| 2011/0207997 A1 | 8/2011 | Greenburg et al. |
| 2011/0230710 A1 | 9/2011 | Hoeg et al. |
| 2012/0010506 A1 | 1/2012 | Ullrich |
| 2012/0071757 A1 | 3/2012 | Salcudean et al. |
| 2012/0136242 A1 | 5/2012 | Qi et al. |
| 2012/0217117 A1 | 8/2012 | Gramann et al. |
| 2012/0306316 A1 * | 12/2012 | Nakamura ......... H01L 41/0973 310/322 |
| 2013/0218024 A1 | 8/2013 | Boctor et al. |
| 2014/0046315 A1 | 2/2014 | Ladtkow et al. |
| 2014/0281961 A1 | 9/2014 | Baker |
| 2015/0032104 A1 | 1/2015 | Howat et al. |
| 2016/0000302 A1 | 1/2016 | Brown et al. |

FOREIGN PATENT DOCUMENTS

| | | |
|---|---|---|
| WO | 9605768 A1 | 2/1996 |
| WO | 97/29684 A1 | 8/1997 |
| WO | 99/32033 A1 | 7/1999 |
| WO | 2004093670 A1 | 11/2004 |
| WO | 2008017051 A2 | 2/2008 |
| WO | 2009073752 A1 | 6/2009 |
| WO | 2012066446 A1 | 5/2012 |
| WO | 2013/038354 A1 | 3/2013 |
| WO | 2013/98715 A1 | 7/2013 |
| WO | 2016010934 A1 | 1/2016 |

* cited by examiner

SURGICAL TOOL WITH FLEX CIRCUIT ULTRASOUND SENSOR

BACKGROUND

Technical Field

The present disclosure relates to a medical instrument including an ultrasound sensor. More particularly, the present disclosure relates to systems and methods that confirm a location of a medical instrument having an ultrasound transducer.

Discussion of Related Art

Electromagnetic navigation (EMN) has helped expand the possibilities of treatment to internal organs and diagnosis of diseases. EMN relies on non-invasive imaging technologies, such as computed tomography (CT) scanning, magnetic resonance imaging (MRI), or fluoroscopic technologies. These images may be registered to a location of a patient within a generated magnetic field, and as a result the location of a sensor placed in that field can be identified with reference to the images. As a result, EMN in combination with these non-invasive imaging technologies is used to identify a location of a target and to help clinicians navigate inside of the patient's body to the target.

In one particular example of currently marketed systems in the area of locating the position of medical instruments in a patient's airway, a sensor is placed at the end of a probe referred to as a locatable guide and passed through an extended working channel (EWC) or catheter, and the combination is inserted into the working channel of a bronchoscope. The EWC and probe with the sensor is then navigated to the target within the patient. Once the target is reached, the locatable guide (i.e., sensor and probe) can be removed and one or more instruments, including biopsy needles, biopsy brushes, ablation catheters, and the like can be passed through the working channel and EWC to obtain samples and/or treat the target. At this point, however, because the locatable guide with the sensor has been removed, the exact location of a distal end of the EWC, and by extension any instrument which might be passed there through is not precisely known. In addition, the precise location within the target tissue is not entirely clear.

Images generated by the non-invasive imaging technologies described above do not provide the resolution of live video imaging. To achieve live video, a clinician may utilize the features of an endoscope. However, an endoscope is limited by its size and as a result cannot be navigated to the pleura boundaries of the lungs and other very narrow passageways as is possible with tools typically utilized in EMN. An alternative is a visualization instrument that is inserted through the EWC and working channel of the endoscope, which can be sized to reach areas such as the pleura boundaries.

As with the locatable guide, however, once the visualization instrument is removed the location of the distal end of the EWC is unclear. One technique that is used is the placement of one or more markers into the tissue near the target and the use of fluoroscopy to confirm location of the EWC and the markers, and any subsequent instruments passed through the EWC. Due to the small diameter of the EWC, simultaneous insertion of more than one instrument may be impractical. Thus, repeated insertions and removals of instruments for visualization, diagnosis, and surgeries are necessitated. Such repeated insertions and removals lengthen diagnostic or surgical time and efforts, and increase costs on patients correspondingly. Thus, it is desirous to make a fewer insertion and/or removal of instruments to shorten times necessary for diagnosis and surgeries while at the same time increasing the certainty of the location of the EWC and instruments passed through the EWC, including imaging modalities.

SUMMARY

Provided in accordance with the present disclosure is a medical instrument including a printed ultrasound sensor. In particular, the medical instrument includes a conductive layer printed circumferentially around at least a portion of a catheter and a nonconductive layer printed on top of the conductive layer. An ultrasound sensor is printed on a distal portion of the nonconductive layer. The ultrasound sensor is adapted to transmit and receive signals. At least one pair of vias are formed in the conductive layer and nonconductive layer and enable an electrical connection between the ultrasound sensor and the conductive layer. In embodiments, the conductive layer is copper, silver, gold, conductive alloys, or conductive polymer. The medical instrument also includes a connector formed on a proximal end of the catheter for connection to an ultrasound image resolution device.

According to aspects of the disclosure, the medical instrument also includes an electromagnetic sensor disposed on a distal portion of the catheter. The medical instrument further includes a base non-conductive layer on the distal portion of the medical instrument on which the electromagnetic sensor is printed.

In embodiments, the ultrasound sensor includes an array of ultrasound transducers. The ultrasound transducers are formed of piezoelectric material. In embodiments, the ultrasound transducers are made at least in part of silicon diaphragms, wherein the piezoelectric material is printed on the silicon diaphragms. The piezoelectric material may be perovskite phase lead zirconate titanate (PZT), quartz, lead titanate, barium titanate, or polyvinylidene fluoride (PVDF). In embodiments, the array of ultrasound transducers are printed in parallel rows of ultrasound transducers.

In another embodiment, the medical instrument is an extended working channel, a biopsy forceps, a biopsy brush, a biopsy needle, or a microwave ablation probe. In further embodiments, the medical instrument includes an outer surface formed of ethylene tetrafluoroethylene (ETFE), polytetrafluoroethylene (PTFE), polyimide, or non-conductive polymer.

According to aspects of the disclosure, the ultrasound sensor, conductive layer, and the non-conductive layer are printed using drop-on-demand (DOD) or ink-jet printing. Additionally, the electromagnetic sensor is printed on a distal portion of the medical instrument.

In another embodiment, the electromagnetic sensor includes at least one pair of contacts electrically connected to the electromagnetic sensor, wherein at least one pair of contacts is coupled to the conductive layer. According to aspects of the disclosure, the conductive layer is connectable to a measurement device configured to sense an induced electrical signal based on a magnetic flux change of an electromagnetic field, wherein a location of the medical instrument in a coordinate system of the electromagnetic field is identified based on the induced electrical signal in the electromagnetic sensor.

BRIEF DESCRIPTION OF THE DRAWINGS

Objects and features of the presently disclosed systems and methods will become apparent to those of ordinary skill in the art when descriptions of various embodiments are read with reference to the accompanying drawings, of which.

Figure 2:
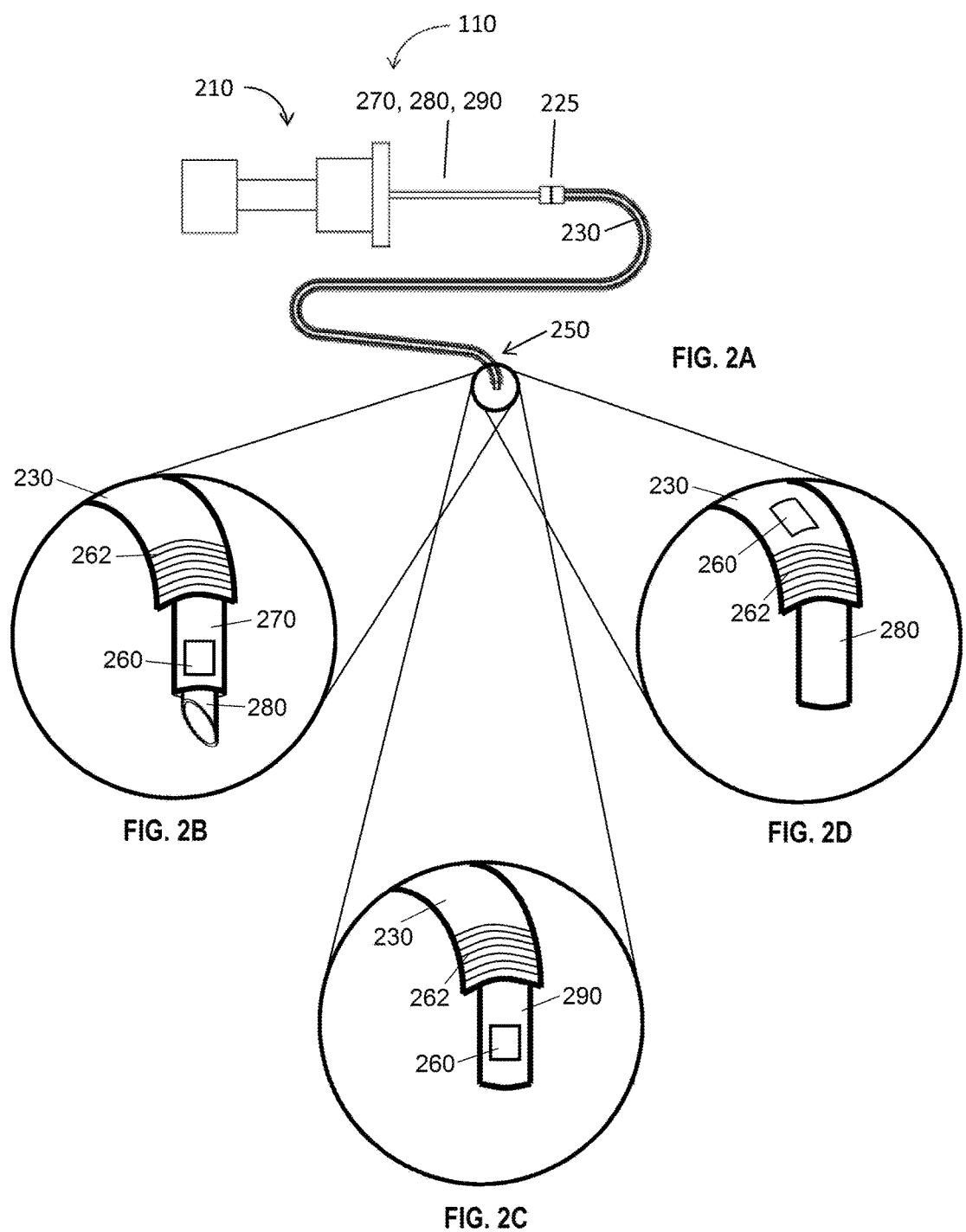
FIG. 2A is a schematic view of a catheter guide assembly and medical instrument in accordance with the present disclosure.
FIG. 2B is an enlarged view of one embodiment of the indicated area of detail of FIG. 2A.
Figure 3:
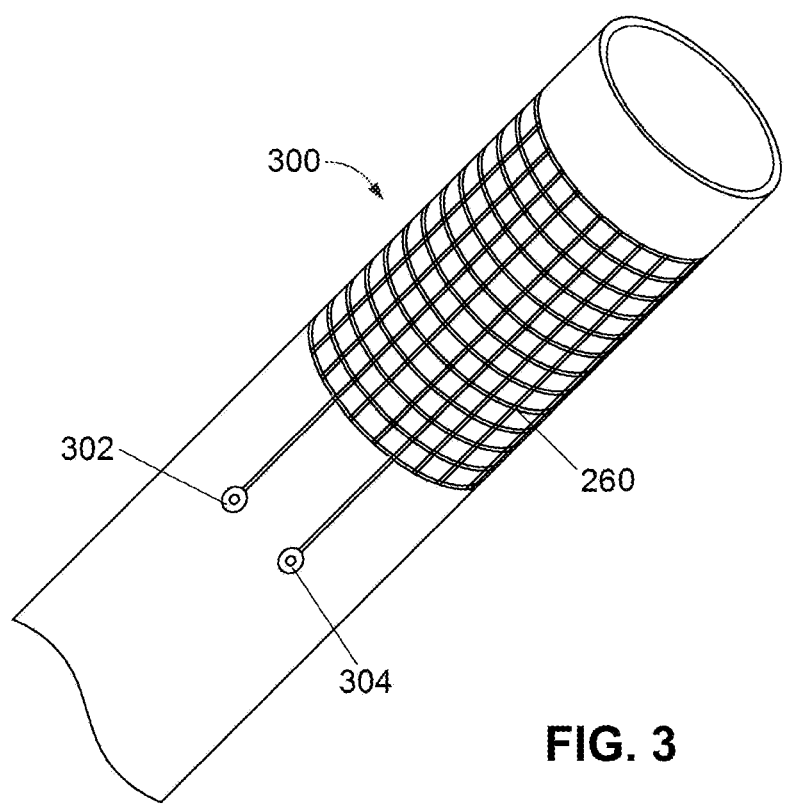
Figure 4:
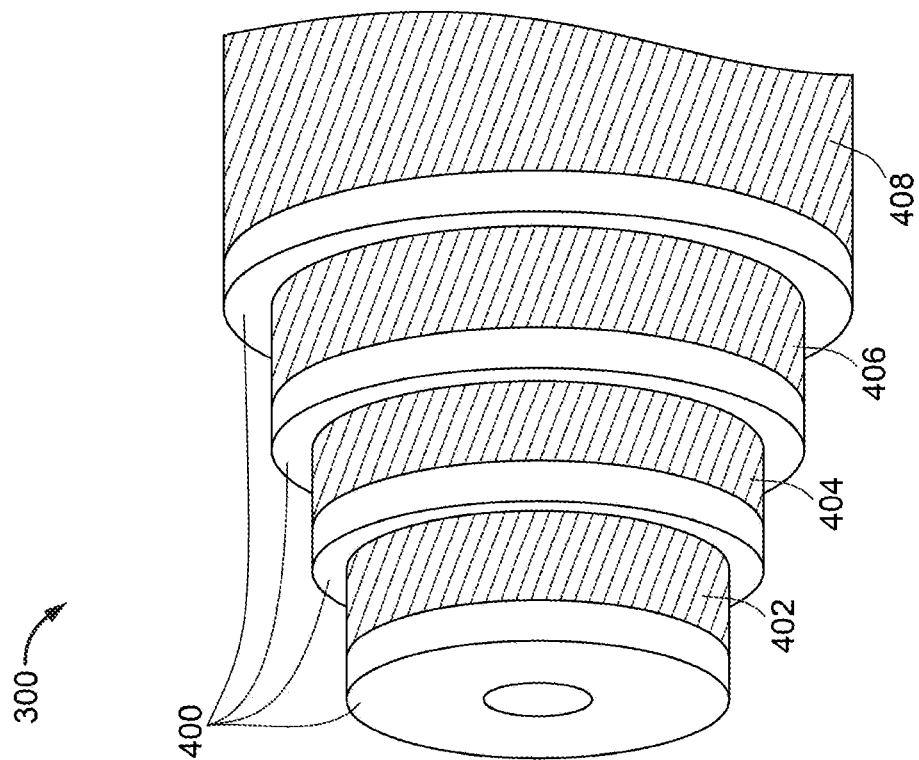
Figure 5A:
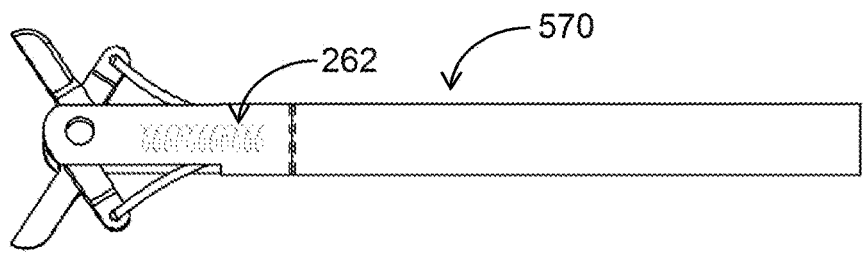
Figure 5B:
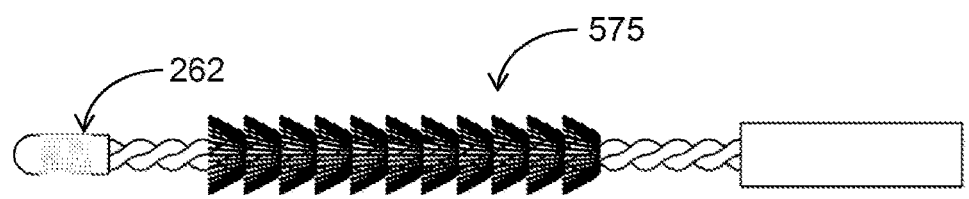
Figure 5C:
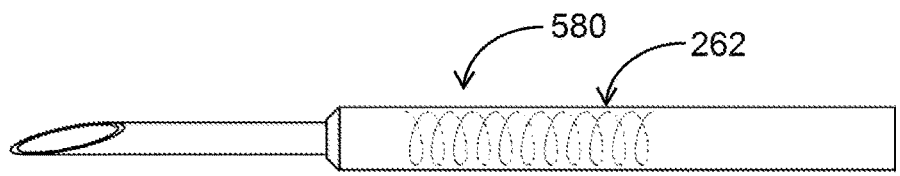
Figure 5D:
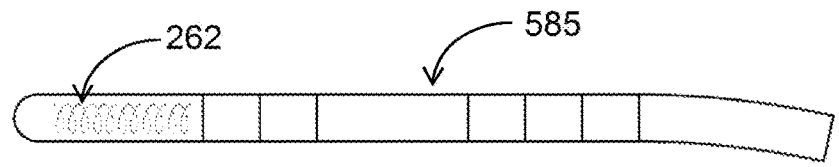
Figure 6:
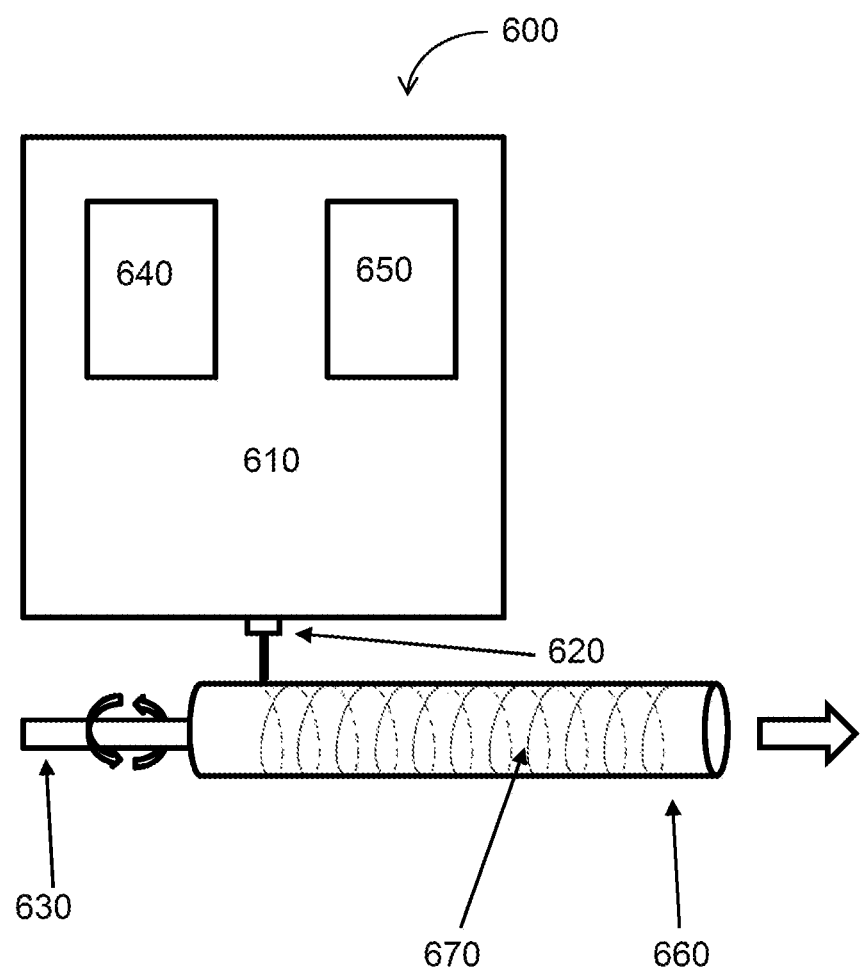
Figure 7:
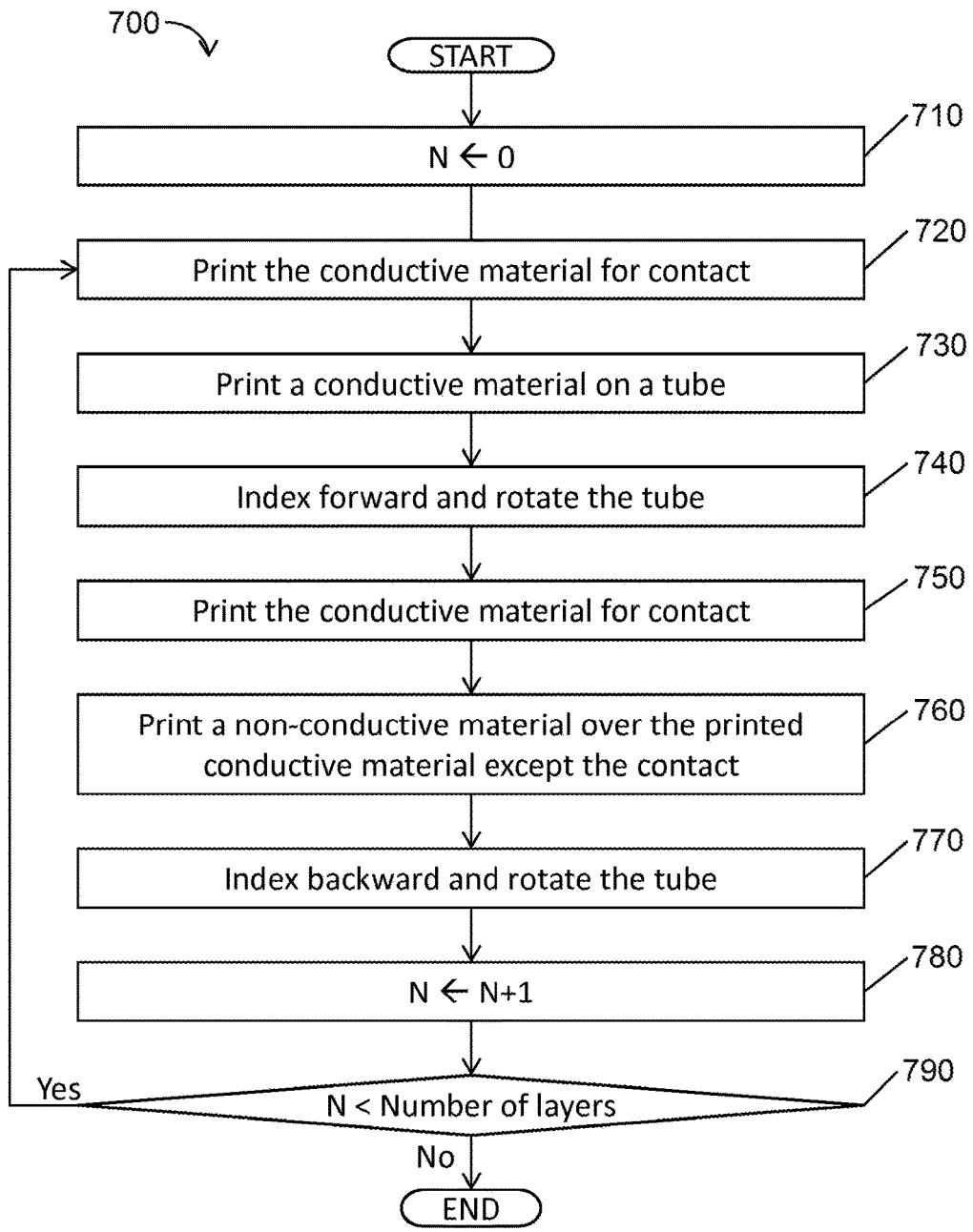

2C is an enlarged view of another embodiment of the indicated area of detail of FIG. 2A;

2D is an enlarged view of yet another embodiment of the indicated area of detail of FIG. 2A;

FIG. 3 depicts a partial perspective view, which illustrates one embodiment of an ultrasound sensor printed at the distal portion of a medical instrument in accordance with an embodiment of the present disclosure;

FIG. 4 is a partial perspective side view of an illustrative design of a proximal portion of a medical instrument around which a series of conductive and nonconductive layers are printed;

FIGS. 5A-5D are partial side views of a plurality of medical instruments in accordance with an embodiment of the present disclosure;

FIG. 6 is schematic illustration of a printer that prints an ultrasound sensor on a surface of a medical instrument in accordance with an embodiment of the present disclosure; and FIG. 7 is a flowchart of a method for printing an ultrasound sensor on a medical instrument in accordance with an embodiment of the present disclosure.

DETAILED DESCRIPTION

The present disclosure is related to medical instruments, systems and methods for identifying a location of medical instruments by using an ultrasound sensor. The ultrasound sensor may be printed directly on or separately fabricated and then affixed to the medical instruments. Since the ultrasound sensor may be inserted inside of patient's body with medical instruments, the location of the medical instrument can be determined in real-time. Further, the sensor may work in conjunction with and/or supplement other imaging modalities. Due to the small size of the ultrasound sensor, medical instruments may incorporate the sensor within the medical instruments, to facilitate continuous navigation. Although the present disclosure will be described in terms of specific illustrative embodiments, it will be readily apparent to those skilled in this art that various modifications, rearrangements, and substitutions may be made without departing from the spirit of the present disclosure. The scope of the present disclosure is defined by the claims appended to this disclosure.

As used herein, the term "distal" refers to the portion that is being described which is further from a user, while the term "proximal" refers to the portion that is being described which is closer to a user. Further, to the extent consistent, any of the aspects and features detailed herein may be used in conjunction with any or all of the other aspects and features detailed herein.

Figure 1:
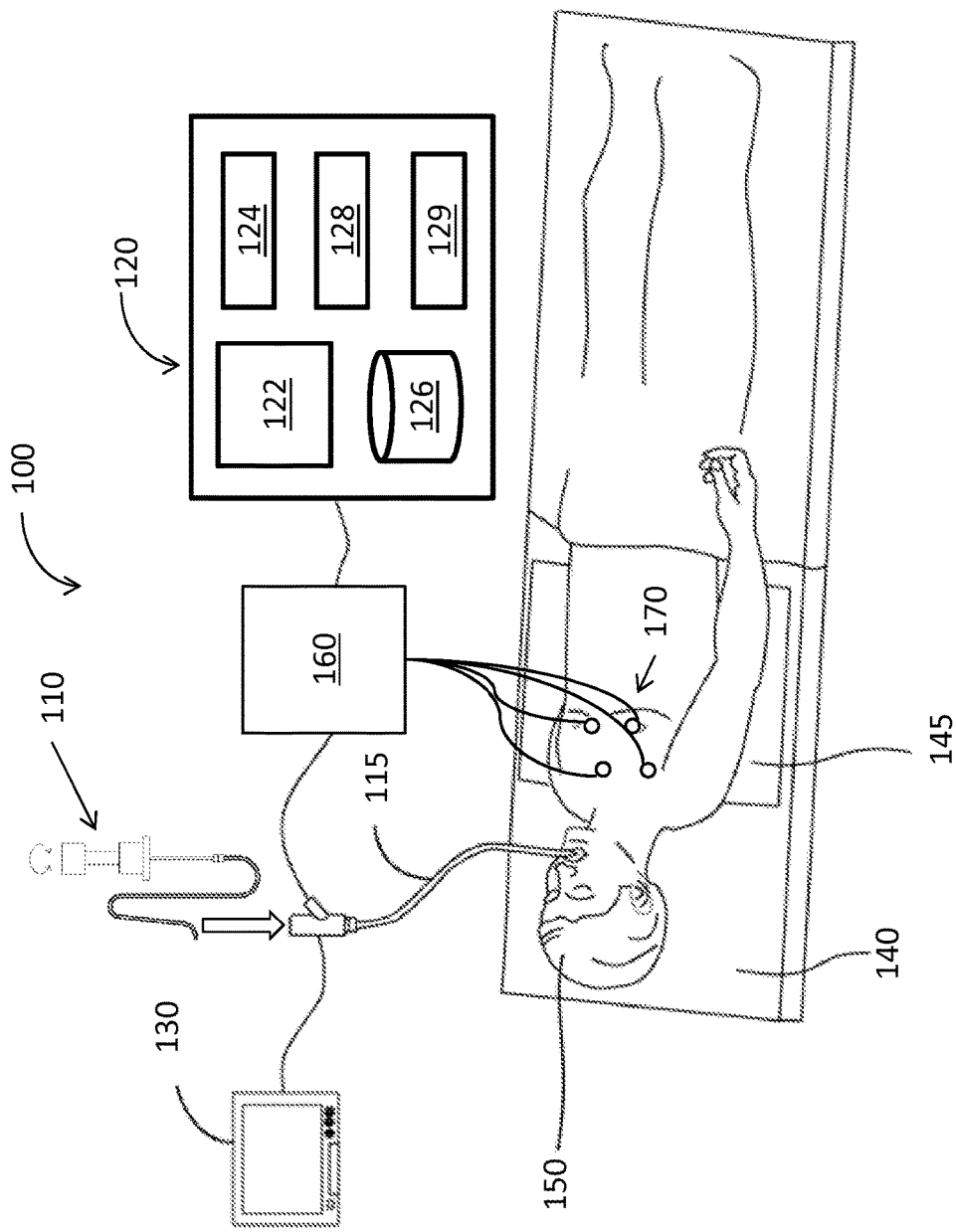
FIG. 1 is a perspective schematic view of a system for identifying a location of a medical instrument in accordance with an embodiment of the present disclosure.

FIG. 1 illustrates one illustrative embodiment of a system and method for identifying a location of medical instruments in an electromagnetic field. In particular, an electromagnetic navigation (EMN) system 100, which is configured to utilize CT, MRI, or fluoroscopic images, is shown. One such EMN system may be the ELECTROMAGNETIC NAVIGATION BRONCHOSCOPY® system currently sold by Medtronic Inc. The EMN system 100 includes a catheter guide assembly 110, a bronchoscope 115, a computing device 120, a monitoring device 130, an electromagnetic (EM) board 145, a tracking device 160, and reference sensors 170. The bronchoscope 115 is operatively coupled to the computing device 120 and the monitoring device 130 via a wired connection (as shown in FIG. 1) or wireless connection (not shown).

FIG. 2A illustrates a schematic illustration of the catheter guide assembly 110 of FIG. 1. The catheter guide assembly 110 includes a control handle 210, which enables advancement and steering of the distal end 250 of the catheter guide assembly 110. The catheter guide assembly 110 may include a catheter 270 inserted in the EWC 230, as shown in FIG. 2B, a locatable guide catheter (LG) 290 inserted in the EWC 230, as shown in FIG. 2C, or a medical instrument 280 inserted in the EWC 230, as shown in FIG. 2D. The catheter 270 may further be configured to receive a medical instrument 280.

In embodiments, the EM sensor 262 can be directly integrated into the distal end of the catheter 270, LG 290, or the EWC 230, as depicted in FIGS. 2B-2D, respectively. In all three embodiments shown in FIGS. 2B-2D, the catheter guide assembly 110 contains an ultrasound sensor (US) 260 at its distal end. Alternatively, in some embodiments, the US sensor 260 may be integrated into the distal end of the catheter 270 or directly on the medical instrument 280. A locking mechanism 225 may secure the catheter 270, the LG 220, or the medical instrument 280 to the EWC 230. The locking mechanism 225 allows a user to know the rotational orientation of the catheter 270, the LG 220, or the medical instrument 280 in addition to its 3-dimensional position. Catheter guide assemblies usable with the instant disclosure may be currently marketed and sold by Medtronic Inc. under the name SUPERDIMENSION® Procedure Kits and EDGE™ Procedure Kits.

For a more detailed description of the catheter guide assemblies, reference is made to commonly-owned U.S. Patent Application Publication Number 2014/0046315 filed on Mar. 15, 2013, by Ladtkow et al. and U.S. Pat. No. 7,233,820, the entire contents of which are incorporated in this disclosure by reference. As will be described in greater detail below, the EM sensor 262 on the distal portion of the LG 290 or EWC 230 senses the electromagnetic field, and is used to identify the location of the LG 290 or EWC 230 in the electromagnetic field, and the US sensor 260 may be used to image the target and confirm the position of the EWC 230, LG 290, and/or the medical instrument 280.

In use, the bronchoscope 115 is inserted into the mouth or through an incision of a patient 150 to capture images of the internal organ. In one embodiment of the EMN system 100, inserted into the bronchoscope 115 is a catheter guide assembly 110 for achieving an access to the lung of the patient 150. The catheter guide assembly 110 may include an extended working channel (EWC) 230 into which a catheter 270 or LG 290 with the EM sensor 262 at its distal portion is inserted. Alternatively, the EWC 230 may have an EM sensor 262 integrated at its distal portion. The EM sensor 262 is used to navigate the EWC 230 through the lung described in greater detail below. Additionally, an US sensor 260 may be integrated at a distal portion of the EWC 230 (as shown in FIGS. 2B-2D) and/or the catheter 270 (not shown) and is used to provide differential imaging information of the surrounding tissue.

In an alternative embodiment, instead of a bronchoscope 115 inserted via a natural orifice, the catheter guide assembly 110 is inserted into the patient 150 via an incision. The catheter guide assembly 110 including the EWC 230 may be inserted through the incision to navigate any luminal network including the airways of a lung and a cardiac luminal network.

The computing device 120, such as, a laptop, desktop, tablet, or other similar computing device, includes a display 122, one or more processors 124, memory 126, a network card 128, and an input device 129. The EMN system 100 may also include multiple computing devices, wherein the separate computing devices are employed for planning, treatment, visualization, and other aspects of assisting clinicians in a manner suitable for medical operations. The display 122 may be touch-sensitive and/or voice-activated, enabling the display 122 to serve as both input and output devices. The display 122 may display two dimensional (2D) images or a three dimensional (3D) model of an internal organ, such as the lung, prostate, kidney, colon, liver, etc., to locate and identify a portion of the internal organ that displays symptoms of diseases.

The display 122 may further display options to select, add, and remove a target to be treated and settable items for the visualization of the internal organ. In an aspect, the display 122 may also display the location of the catheter guide assembly 110 in the electromagnetic field based on the 2D images or 3D model of the internal organ. In another aspect, the display 122 may also display a live ultrasound image captured by the US sensor 260. This live ultrasound image may be superimposed over the 2D images or 3D model of the organs or over a virtual bronchoscopy image, or over a fluoroscopy image, or it may be displayed in a side-by-side configuration. In another embodiment, a separate display 122 may be used to display the ultrasound image.

The one or more processors 124 execute computer-executable instructions. The processors 124 may perform image-processing functions so that the 3D model of the internal organ and/or the ultrasound image can be displayed on the display 122. In embodiments, the computing device 120 may further include a separate graphic accelerator (not shown) that performs only the image-processing functions so that the one or more processors 124 may be available for other programs. The memory 126 stores data and programs. For example, data may be image data for the 3D model, ultrasound imaging, or any other related data such as patients' medical records, prescriptions and/or history of the patient's diseases.

One type of program stored in the memory 126 is a 3D model and pathway planning software module (planning software). An example of the 3D model generation and pathway planning software may be the EMN planning software currently sold by Medtronic Inc. When image data of a patient, which is typically in digital imaging and communications in medicine (DICOM) format, from for example a CT image data set (or an image data set by other imaging modality) is imported into the planning software, a 3D model of the internal organ is generated. In an aspect, imaging may be done by CT imaging, magnetic resonance imaging (MRI), functional MRI, X-ray, and/or any other imaging modalities. To generate the 3D model, the planning software employs segmentation, surface rendering, and/or volume rendering. The planning software then allows for the 3D model to be sliced or manipulated into a number of different views including axial, coronal, and sagittal views that are commonly used to review the original image data. These different views allow the user to review all of the image data and identify potential targets in the images.

Once a target is identified, the software enters into a pathway planning module. The pathway planning module develops a pathway plan to achieve access to the targets and the pathway plan pin-points the location and identifies the coordinates of the target such that they can be arrived at using the EMN system 100, and particularly the catheter guide assembly 110 together with the EWC 230 and the LG 290. The pathway planning module guides a clinician through a series of steps to develop a pathway plan for export and later use during navigation to the target in the patient 150. The term, clinician, may include doctor, surgeon, nurse, medical assistant, or any user of the pathway planning module involved in planning, performing, monitoring and/or supervising a medical procedure.

Details of these processes and the pathway planning module can be found in U.S. Patent Application Publication Number 2014/0281961 filed by Medtronic Inc. on Jun. 21, 2013, and entitled "Pathway Planning System and Method," the entire contents of which are incorporated in this disclosure by reference. Such pathway planning modules permit clinicians to view individual slices of the CT image data set and to identify one or more targets. These targets may be, for example, lesions or the location of a nerve which affects the actions of tissue where the disease has rendered the internal organ's function compromised.

The memory 126 may store navigation and procedure software which interfaces with the EMN system 100 to provide guidance to the clinician and provide a representation of the planned pathway on the 3D model and 2D images derived from the 3D model. An example of such navigation software is the ILOGIC® navigation and procedure suite sold by Medtronic, Inc. In practice, the location of the patient 150 in the EM field generated by the EM field generating device 145 must be registered to the 3D model and the 2D images derived from the 3D model. Such registration may be manual or automatic and is described in detail and commonly assigned U.S. patent application Ser. No. 14/753,288 entitled "System and method for navigating within the lung," the entire contents of which are incorporated in this disclosure by reference.

As shown in FIG. 1, the patient surface or bed 140 is configured to provide a flat surface for the patient to lie down and includes an EM field generating device 145. When the patient 150 lies down on the EM board 145, the EM field generating device in the EM board 145 generates an EM field sufficient to surround a portion of the patient 150. The EM sensor 262 at the end of the LG 290 is used to determine the location of the distal end of the LG 290 and therewith the EWC 230 within the patient. In an aspect, a separate EM sensor 262 may be located at the distal end of the EWC 230 and therewith the exact location of the EWC 230 in the EM field generated by the EM field generating device 145 can be identified within the patient 150.

In yet another aspect, the EM board 145 may be configured to be operatively coupled with the reference sensors 170 which are located on the chest of the patient 150. The reference sensors 170 move up following the chest while the patient 150 is inhaling and move down following the chest while the patient 150 is exhaling. The movement of the chest of the patient 150 in the EM field is captured by the reference sensors 170 and transmitted to the tracking device 160 so that the breathing pattern of the patient 150 may be recognized. The tracking device 160 also receives the output of the EM sensor 262, combines both outputs, and compensates the breathing pattern for the location of the EM sensor 262. In this way, the location identified by the EM sensor 262 may be compensated for such that the compensated location of the EM sensor 262 may be synchronized with the 3D model of the internal organ. As noted above, however, the use of an LG 290 with an EM sensor 262 at its distal end 250 can result in challenges surrounding instrument swaps, loss of location information, and a general prolongation of the time needed for a procedure. To alleviate these issues, the EM sensor 262 may be printed directly on the distal portion of a medical instrument 280 or the EWC 230 as described in U.S. Provisional Patent Application No. 62/170,383 filed by Medtronic Inc. on Jun. 3, 2015, and entitled "Medical Instrument with Sensor for use in a System and Method for Electromagnetic Navigation," the entire contents of which are incorporated in this disclosure by reference. Additionally, a US sensor 260 may be printed directly on the distal portion of a medical instrument 280, catheter 270, and/or EWC 230. When used in conjunction with the EM sensor 262, the US sensor 260 improves accuracy and precision when navigating to a target tissue by providing real time imaging of the distal end of the medical instrument 280, catheter 270, and/or EWC 230.

FIG. 3 depicts an embodiment of an US sensor 260 printed on an instrument 300. The instrument 300 may be an EWC 230, a catheter 270, a medical instrument 280, a biopsy instrument, an ablation instrument, a monopolar or bipolar electrosurgical instrument, a marking instrument, or a needle, in short any instrument capable of being inserted into the luminal network (e.g., the airways or vasculature of a patient). In one embodiment the instrument 300 is sized to pass through the EWC 230. Alternatively, the instrument 300 may be the EWC 230. Other exemplary instruments 300 are shown in FIGS. 5A-5D, depicting biopsy forceps 570, a biopsy brush 575, a biopsy needle 580, and a microwave ablation probe 585, each having an US sensor 260 applied by the methods of the present disclosure. The US sensor 260 can provide ultrasound imaging of tissue at the distal end of instrument 300. When used in conjunction with an EM sensor 262, a user is able to identify the location of the instrument 300 (through the EM sensor 262) and obtain a visual image of the precise location of the instrument 300 (through the US sensor 260). Any number of combinations for the location of the US sensor 260 and EM sensor 262 are envisioned. For example, some of which have been discussed above, the US sensor 260 may be located on the EWC 230 and the EM sensor 262 on the instrument 300, or the US sensor 260 may be located on the instrument 300 and the EM sensor 262 on the EWC 230. Alternatively, both the US sensor 260 and the EM sensor 262 may be located on either the EWC 230 or the instrument 300.

As will be described in greater detail below, the distal portion of the instrument 300 may be made of or covered by Ethylene tetrafluoroethylene (ETFE), Polytetrafluoroethylene (PTFE), polyimide, or another suitable material to form a non-conductive base for the US sensor 260. If the distal portion of the instrument 300 is not covered or made of a non-conductive material, a non-conductive material may be applied to the distal portion first to form an insulating base for the US sensor 260. In embodiments, instrument 300 may comprise a hollow tube consisting of an inner PTFE liner. The PTFE liner provides lubricity for easy sliding of tools down the center of the instrument 300. In one embodiment, the EM sensor 262 is printed directly on the PTFE layer. Radially outward of the PTFE layer is a wire braid layer (not shown). The wire braid helps provide structural integrity and torquability to allow for easy maneuverability of the instrument 300. The final layer is a thermal plastic layer which, through a heat process, bonds all three layers together to provide durability.

With respect to the US sensor 260 depicted in FIG. 3, the US sensor 260 may be printed in an array. Although FIG. 3 depicts the US sensor 260 printed in perpendicular rows, other configurations are envisioned. For example, the US sensor 260 may be printed in non-overlapping parallel rows (as depicted in FIGS. 2B-2D) or in non-perpendicular rows. The US sensor 260 is printed from piezoelectric material. In embodiments, an EM sensor 262 (shown in FIGS. 2B-D) is also printed on the instrument 300 adjacent to the US sensor 260. PZT is a preferred material due to its strong mechanical to electrical coupling. The US sensor 260 may be fabricated and printed on the medical instrument 300 using known microelectromechanical system (MEMS) and/or nanoelectromechanical system (NEMS) techniques. In one embodiment, the US sensor 260 includes an array of clamped silicon diaphragms (not shown), which are a common component of US sensors. In particular, a thin layer of piezoelectric material, sandwiched between two electrodes, is printed on the silicon diaphragms.

In embodiments, the radius of the electrodes is smaller than the radius of the diaphragm. When an AC driving signal is applied between the electrodes, the resulting strain on the piezoelectric material vibrates the structure and diaphragm sending ultrasonic pressure waves into its surroundings. Alternatively, the US sensor 260 may be exposed to ultrasonic pressure waves from its surrounding environment, and these waves are translated into electrical signals.

In embodiments, the US sensor 260 may be printed in an array of US sensors coupled together using known printing techniques, such as drop-on-demand (DOD) or ink-jet printing. The US sensor 260 and the EM sensor 262 may be printed adjacent each other or they may be printed in layers. Specifically, the EM sensor 262 is first printed on the instrument 300, a non-conductive material is than applied over the EM sensor 262, and the US sensor 260 is printed on the non-conductive material. It is envisioned that any number of layers and/or combination of sensors may be printed on the instrument 300. Each sensor may have a different configuration or location, e.g., a different orientation, a different length L, and a different distance from the distal end of the instrument 300.

In accordance with the present disclosure, US sensor 260 may be printed directly onto the instrument 300. That is, during the manufacture of the instrument 300, one of the processing steps is to apply one or more conductive inks, piezoelectric material, or other materials to the instrument 300. This printing may be performed by a number of processes including ink jet printing, flexographic printing, vapor deposition, etching, and others known to those of skill in the art without departing from the scope of the present disclosure. The US sensor 260 may have a thickness of about 0.01 to about 0.05 millimeter (mm) so that the sensor can be printed on an instrument 300 without appreciably increasing its dimensions. In accordance with one embodiment, a final non-conductive layer covers the US sensor 260, thereby protecting the top layer of the US sensor 260. In some embodiments, the non-conductive material may be Kapton, ETFE, PTFE, non-conductive polymer, or polyimide.

As depicted in FIG. 3, the US sensor 260 contains vias 302, 304 connected to the terminals of US sensor 260. In embodiments, each via is electrically coupled to a different conductive layer on the proximal portion of the instrument 300, as shown in more detail in FIG. 4. Although not shown, EM sensor 262 may also contain one or more respective vias.

FIG. 4 depicts an embodiment of a proximal portion of an instrument 300 and the various layers of conductive and/or nonconductive material printed directly onto the instrument. FIG. 4 is not drawn to scale and is meant for illustrative purposes only. Each layer of conductive and/or nonconductive material may range in thickness from 9 microns to 0.05 millimeters (mm).

As described above, the EM sensor 262 and US sensor 260 printed on the distal portion of instrument 300. On the proximal portion of the instrument 300, nonconductive layers 400 and conductive layers 402, 404, 406, 408 are printed directly on the PTFE layer in layers in alternating fashion. In other words, a base nonconductive layer 400 is printed on top of the PTFE layer followed by a conductive layer 402 printed on top of the base nonconductive layer. Another nonconductive layer is then printed on top of conductive layer 402 and another conductive layer 404 is printed on top of the nonconductive layer. This process is then repeated until a desired number of nonconductive and conductive layers are achieved. In embodiments, the final layer is a nonconductive layer and a thermal plastic layer is then placed on top of the final nonconductive layer. The embodiment shown in FIG. 4 illustrates a total of four conductive layers 402, 404, 406, 408 and four nonconductive layers 400. A final nonconductive layer (not shown) may be printed on the final conductive layer 408. In aspects, the conductive material may be copper, silver, gold, conductive alloys, or conductive polymer, and the non-conductive material may be Kapton, ETFE, PTFE, non-conductive polymer, or polyimide.

The conductive layers function as wires and form a return path for the US sensor 260 and EM sensor 262, connecting the sensors to tracking device 160 and/or computing device 120. For example, in one embodiment, conductive layer 402 is connected to via 302, conductive layer 404 is connected to via 304 of US sensor 260, and conductive layer 402 and conductive layer 404 are coupled to the EM sensor 262 through vias (not shown).

Since the US sensor 260 and EM sensor 262 are very thin, they have a high resistance, however, a low resistance is desired for the return path. In one embodiment, each conductive layer 402, 404, 406, 408 is printed 360 degrees around the instrument 300 and along the length of the instrument 300 back to the proximal end in order to reduce the resistance on the return path.

As described above, one methodology for applying US sensors to instruments is via printing directly on the instruments. FIG. 6 shows a printing apparatus 600 that prints conductive material, non-conductive material, and piezoelectric material directly to the desired locations of the instruments. The printing apparatus 600 includes a reservoir 610, a printing nozzle 620, and an actuating arm 630. The reservoir 610 includes a first tank 640, which contains a conductive material or a piezoelectric material, and a second tank 650, which contains a non-conductive material. The printing apparatus 600 can print a circuit on any instrument 660, which can be locked into the distal end of the actuating arm 630. In an aspect, the printing apparatus may print a sensor over a polymer.

A controller (not shown) of the printing apparatus 600 controls an actuating motor (not shown) to move the actuating arm 630. The actuating motor is fixedly connected to the proximal end of the actuating arm 630. The actuating motor can index forward and backward and rotate the actuating arm 630. In an aspect, the actuating motor may move the reservoir 610 while printing. For example, the actuating motor may index forward or backward the reservoir 610 while rotating the actuating arm 630. Still further, the reservoir 610 and instrument 660 may be held motionless while the printing nozzle 620, which is fluidly connected to the reservoir 610, moves about the instrument 660. Further, combinations of these techniques may be employed by those of skill in the art without departing from the scope of the present disclosure.

In an aspect, the printing may be started from the distal end of the instrument 660 or the proximal end of the instrument 660. In a case when the printing is started from the distal end of the instrument 660, the actuating arm 630 indexes the instrument 660 forward so that the printing nozzle 620 can print the conductive material toward the proximal end of the instrument 660. In another case when the printing is started from the proximal end of the instrument 660, the actuating arm 630 indexes the instrument 660 backward so that the printing nozzle 620 can print the conductive material toward the distal end of the instrument 660. After completion of printing the non-conductive material, the printing nozzle 620 may print the conductive material or piezoelectric material over the instrument 660 again. By repeating these steps, the instrument 660 may have several types of sensors.

FIG. 7 shows a method 700 of printing the conductive layers 402, 404, 406, 408 which form the return paths for the US sensor 260 and EM sensor 262 on a surface of the instrument 660. The method 700 starts from setting a counter N as zero in step 710. In step 720, the printer prints the conductive material for the vias 302, 304 or for the electrical contacts which couple to an external computing device or ultrasound image resolution device. In step 730, the printer prints a conductive material on the tube. While printing, in step 740, an indexing arm of the printer, which holds the tube, indexes forward or backward, and rotates the tube.

In step 750, the printer prints the conductive material for another electrical contact. The contacts printed in steps 710 and 750 are to be used to connect to wires which lead to and connect with an external apparatus such as the tracking device 160 of FIG. 1 or an ultrasound image resolution device.

In step 760, the printer prints a non-conductive material to form a non-conductive film over the printed conductive material. While printing the non-conductive material, in step 770, the actuating arm of the printer indexes forward or backward and rotates in a direction reverse from the direction of printing the conductive material. In this way, the printed conductive material is insulated from or protected from other environments.

In step 780, the counter N is incremented by one. In step 790, the counter N is compared with a predetermined number of layers. If the counter N is less than the predetermined number of layers, the method 700 repeats steps 720 through 790. If the counter N is not less than the predetermined number of layers, the method is ended.

Although embodiments have been described in detail with reference to the accompanying drawings for the purpose of illustration and description, it is to be understood that the inventive processes and apparatus are not to be construed as limited. It will be apparent to those of ordinary skill in the art that various modifications to the foregoing embodiments may be made without departing from the scope of the disclosure.

What is claimed is:

1. A medical instrument comprising:
   a catheter;
   a first conductive layer printed circumferentially around at least a portion of the catheter;

a first nonconductive layer printed on the first conductive layer;
a second conductive layer printed circumferentially around at least a portion of the first nonconductive layer;
a second nonconductive layer printed on the second conductive layer;
an ultrasound sensor printed circumferentially around a distal portion of the second nonconductive layer, the ultrasound sensor adapted to transmit and receive signals;
a first via connecting the ultrasound sensor to the first conductive layer;
a second via connecting the ultrasound sensor to the second conductive layer; and
a connector formed on a proximal end of the catheter for connection to an ultrasound image resolution device.

2. The medical instrument according to claim 1, further comprising:
an electromagnetic sensor disposed on a distal portion of the catheter; and
a third conductive layer spaced apart from the first and second conductive layers.

3. The medical instrument according to claim 2, wherein the third conductive layer is connectable to an electromagnetic tracking device configured to sense an induced electrical signal based on a magnetic flux change of an electromagnetic field, wherein a location of the medical instrument in a coordinate system of the electromagnetic field is identified based on the induced electrical signal in the electromagnetic sensor.

4. The medical instrument according to claim 2, further comprising:
a fourth conductive layer spaced apart from the first, second and third conductive layers.

5. The medical instrument according to claim 1, wherein the ultrasound sensor comprises an array of ultrasound transducers.

6. The medical instrument according to claim 5, wherein the array of ultrasound transducers comprises a piezoelectric material.

7. The medical instrument according to claim 6, wherein the array of ultrasound transducers further comprises silicon diaphragms, wherein the piezoelectric material is printed on the silicon diaphragms.

8. The medical instrument according to claim 6, wherein the piezoelectric material is selected from the group consisting of perovskite phase lead zirconate titanate (PZT), quartz, lead titanate, barium titanate, and polyvinylidene fluoride (PVDF).

9. The medical instrument according to claim 5, wherein the array of ultrasound transducers comprises printed parallel rows of ultrasound transducers.

10. The medical instrument according to claim 1, wherein the medical instrument is selected from the group consisting of an extended working channel, a biopsy forceps, a biopsy brush, a biopsy needle, and a microwave ablation probe.

11. The medical instrument according to claim 1, wherein the first or second conductive layer is formed from a material selected from the group consisting of copper, silver, gold, conductive alloys, and conductive polymer.

12. The medical instrument according to claim 1, wherein the first or second nonconductive layer is formed of a material selected from the group consisting of ETFE, PTFE, polyimide, and non-conductive polymer.

13. The medical instrument according to claim 1, wherein the ultrasound sensor, the first or second conductive layer, and the first or second nonconductive layer are printed using drop-on-demand (DOD) or ink-jet printing.

14. The medical instrument according to claim 1, wherein the first via or the second via is formed at a distal portion of the catheter.

15. A catheter guide assembly comprising:
an extended working channel defining a lumen; and
a catheter positionable through the lumen of the extended working channel, the catheter comprising:
a first conductive layer;
a first nonconductive layer disposed on the first conductive layer;
a second conductive layer disposed on the first nonconductive layer;
a second nonconductive layer disposed on the second conductive layer;
an ultrasound sensor printed circumferentially around a distal portion of the second nonconductive layer;
a first via connecting the ultrasound sensor to the first conductive layer; and
a second via connecting the ultrasound sensor to the second conductive layer.

16. The catheter guide assembly of claim 15, wherein the ultrasound sensor has a thickness of from 0.01 mm to 0.05 mm.

17. The catheter guide assembly of claim 15, further comprising an electromagnetic sensor disposed at a distal portion of the extended working channel.

18. A catheter comprising:
a first conductive layer connectable to an electromagnetic tracking device configured to sense an induced electrical signal based on a magnetic flux change in an electromagnetic field;
a first nonconductive layer disposed on the first conductive layer;
a second conductive layer disposed on the first nonconductive layer;
a second nonconductive layer disposed on the second conductive layer;
an ultrasound sensor printed circumferentially around a distal portion of the second nonconductive layer, the ultrasound sensor having a thickness of from 0.01 mm to 0.05 mm;
a first via connecting the ultrasound sensor to the second conductive layer; and
a second via connecting the ultrasound sensor to a third conductive layer,
wherein a location of the catheter in a coordinate system of the electromagnetic field is identifiable based on the induced electrical signal.

* * * * *